United States Patent [19]

Schmidt

[11] Patent Number: 4,463,757

[45] Date of Patent: Aug. 7, 1984

[54] COVERING DEVICE FOR TRACHEOSTOMY STOMA

[76] Inventor: Edward J. Schmidt, 774 LaFond Ave., St. Paul, Minn. 55104

[21] Appl. No.: 374,486

[22] Filed: May 3, 1982

[51] Int. Cl.³ .............................................. A62B 7/10
[52] U.S. Cl. .......................... 128/205.29; 128/206.19; 128/207.11; 128/DIG. 15
[58] Field of Search ...................... 128/205.27, 205.29, 128/207.14, 207.17, 206.12, 207.11, 206.13, 206.14, 206.16, 206.19, 201.13, 206.17

[56] References Cited

U.S. PATENT DOCUMENTS

| 537,678 | 4/1895 | Détourbe | 128/206.16 |
|---|---|---|---|
| 681,622 | 8/1901 | Cover | 128/206.12 |
| 787,167 | 4/1905 | Gates | 128/206.16 |
| 2,491,647 | 12/1949 | Colavita | 128/275 |
| 3,014,479 | 12/1961 | Matheson | 128/206.15 |
| 3,137,296 | 6/1964 | Gurtowski | 128/206.12 |
| 3,216,415 | 11/1965 | Littleton | 128/206.17 |
| 3,330,271 | 7/1967 | Hozier | 128/140 |
| 3,464,410 | 9/1969 | Buchanan | 128/205.29 |
| 3,811,436 | 5/1974 | Ferrell | 128/140 |
| 3,884,227 | 5/1975 | Lutz et al. | 128/146.2 |
| 3,920,009 | 11/1975 | Olsen | 128/140 R |
| 4,141,703 | 2/1979 | Mulchi | 128/206.15 |
| 4,378,012 | 3/1983 | Brown | 128/207.17 |

Primary Examiner—Henry J. Recla
Attorney, Agent, or Firm—Anthony G. Eggink

[57] ABSTRACT

The tracheostomy stoma covering device is for filtering and conditioning the air inhaled through the stoma. The device includes an encasement member having generally flexible mesh front and back panels, and having access means for entry into the interior thereof. Flexible strap means extend from generally the top side portions of the encasement member for securing the device about a wearer's neck with the encasement member covering the stoma. Within the interior of the encasement member is a replaceable air filter means which is exchangable through the access means. Additionally, a moisture absorbing and releasing and heat absorbing and releasing element is provided for placement within the encasement member for selective use depending upon environmental factors. Adjustable strap means are provided for a wide range of user neck sizes, and strap placement and configurations are disclosed to ensure comfortable wear and proper location of the device relative to the stoma. And, formable or malleable strip means are used in encasement member border sections to permit the encasement member to be contoured to fit the configuration of a user's neck. Additionally, one embodiment of the device has a removable front panel member to permit the selection of a plurality of different colored front panel members to be used with the remaining device portions so that the device can become inconspicuously matched with a wearer's clothing.

20 Claims, 4 Drawing Figures

COVERING DEVICE FOR TRACHEOSTOMY STOMA

This invention relates to a device for covering a stoma, produced as a result of a surgical tracheostomy procedure. Particularly, this invention relates to a device for filtering and conditioning the air inhaled through this stoma.

The surgical performance of tracheostomies has become increasingly necessary due to various diseases and related breathing difficulties. As a result of this procedure, a patient receives a stoma at the anterior lower neck through which subsequent respiration takes place. However, the by-passed nose and mouth functions for breathing purposes has caused much discomfort and medical problems to these patients. Particularly, the losses of inhaled air filtering, moisture transfer and heat transfer functions continually plague these patients, and often increase their susceptibility to infections. The character or variety of sputum which is often expelled through the stoma by many patients indicates this infectious activity.

The tracheostomy stoma covering device of this invention provides a wearer with air filtering means for the air inhaled through the stoma, and with air conditioning means, from a moisture and heat standpoint, of this filtered air. Additionally, the device of this invention permits the user to filter and condition the inhaled air in accordance with prevailing environmental conditions.

Several types of filter devices for tracheal use have been utilized or proposed in the past. However, these devices have been complex in design, limited in use and effectiveness, or have been difficult for a user to wear. For example, some devices are designed to fit directly into the stoma. However, during a tracheostomy procedure it is often found that varying stoma diameters are necessary, and, therefore, making specifically diameter sized stoma devices difficult to properly fit.

Still other devices are designed particularly for sputum discharges, are bulky in design, and cumbersome for wearers. And, other devices, although designed for air filtering purposes, do not permit a user to condition the inhaled air for moisture and temperature purposes. With respect to the latter devices, they are often of the knitted, cloth-pad type which are tied about a user's neck. These respiratory pads are commonly distributed through the Lost Chord Club, an organization of individuals having had lyryngectomies, surgical procedures involving tracheostomies.

Tracheostomy stoma covering devices according to this invention overcome the problems, difficulties and shortcomings of those prior art devices discussed above. The tracheostomy stoma covering devices according to the invention are useful to provide a user, having had a tracheostomy, with a device which is comfortable to wear, easy to clean, inexpensive to manufacture, and versatile in use. The devices of this invention provide a wearer with an adjustable device which securely covers the stoma, and which is able to accomodate a range of neck sizes. And, despite the long-standing need for an effective, versatile, and comfortably worn stoma covering device for a user having had a tracheostomy, none in so far as is known has been developed. An effective, inexpensive, comfortable to wear, easy to clean and maintain, tracheostomy stoma covering device, and one which is versatile to accomodate verying environmental conditions, in terms of air filtering ability and moisture and temperature conditioning requirements, is provided by the teachings of this invention. And, with respect to the latter, this device permits a user to breathe comfortably, without dryness of the mucous membranes, and to prevent or control coughing spasms and the susceptibility to infectious diseases.

In summary, this invention provides an air filtering and conditioning device for covering a stoma of a wearer having had a tracheostomy. The device includes a washable encasement member having generally flexible mesh front and back panels. Additionally, the encasement member has access means into the interior thereof. Extending from the top, side portions of the encasement member are washable strap means, having adjustable fastener means at their respective ends, for securing the device about a user's neck.

A replacable air filter means for coextensive placement with the flexible mesh portions of the front and back panels of the encasement member is provided to filter the incoming air inhaled through the stoma. And, this air filtering means is replacable, as necessary, through the access means of the encasement member.

In use, the tracheostomy stoma covering device is placed with the back panel of the encasement member covering the stoma of a user. The device is secured in this position by adjusting and communicating the mating fastener means of the strap means about the user's neck.

Also provided by the invention is an encasement member having border portions about its periphery. Within the upper and opposing side portions of the border are secured, formable or malleable strips which when formed permit the user to contour the encasement member to the configuration of the neck. And, this provides an effective seal to contaminants entering the stoma, and ensures that all the incoming air is properly filtered and conditioned.

Additionally provided by the invention is a moisture absorbing and releasing member for placement within the encasement member between the back panel mesh and the air filtering means. This member, which is a cellular foam member of synthetic construction, permits the utilization of cellulose or paper air filters which are inexpensive, and, thus, daily changable, by protecting the paper filter from sputum and the moisture laden air expelled from the wearer's lungs. Additionally, this foam member serves as a moisture absorbing and transfer source to the subsequently inhaled air to the lungs of the wearer.

When environmental conditions dictate, a heat absorbing and releasing element is also placeable within the encasement member of the device through the access means. This air conditioning element permits further absorption of heat from the air expelled through the stoma, and, subsequently, permits the transfer of the absorbed heat to the inhaled air. This pre-warming of the incoming air function greatly increases the comfort of the device wearer when outside temperatures are low. The access means of the encasement member permits the removal, exchange, and/or addition of such air conditioning elements, for moisture and heat transfer purposes, to particularly suit the environmental conditions that exist. Thus, in Summer, the need for only a moisture exchange element and an air filter element may exist, while in Winter, a relatively thick element for moisture and heat transfer purposes may be required in addition to the air filter means.

And, provided by the invention are strap means which extend generally diagonally upward from the encasement member to ensure proper stoma coverage of the device. And, elastic portions are provided which extend from the opposing top portions of the encasement member to intersect and connect with the strap means. These elastic portions permit the device to be comfortably worn about the user's neck, and permits the user to freely rotate the neck without fear of shifting the encasement member relative to the stoma.

And, finally provided by this invention are encasement member access means which consist of Velcro fastener elements, which are washable and which permit the easy exchange, addition or removal of the various air filter and air conditioning elements placed therein. And, one embodiment of the device provides a totally seperable encasement member which permits a plurality of colored front panel members to be utilized with the remaining device elements, so that a user is able to match a front panel member with other clothing to make the device relatively inconspicuous when worn.

These and other benefits of this invention will become clear from the following description by reference to the drawings, wherein.

Figure 3:
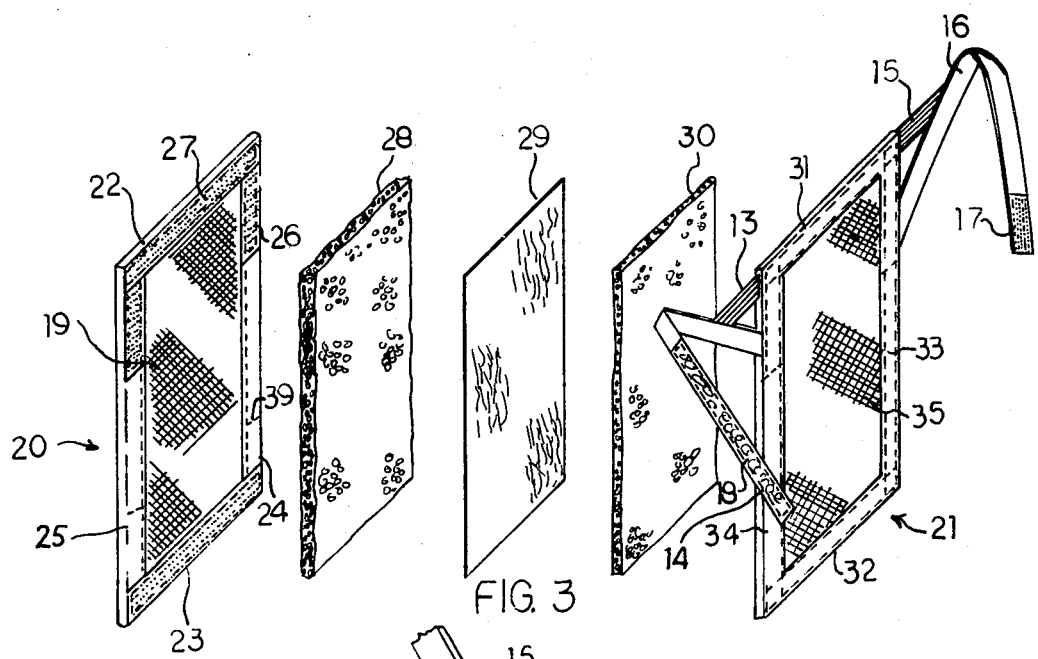
Figure 4:
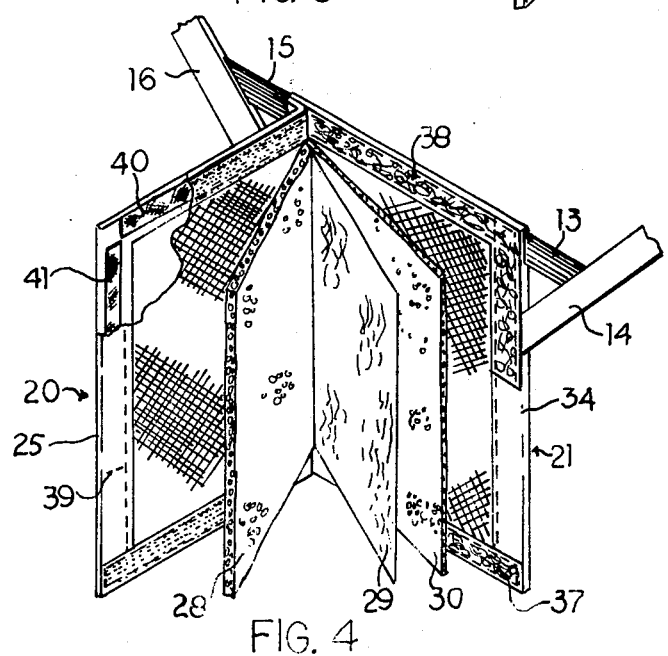

FIG. 3 is a schematic, perspective view of a tracheostomy stoma covering device of this invention, and which illustrates the various and respective air filtering and air conditioning elements of one embodiment of the device; and, FIG. 4 is a schematic, perspective view of another embodiment of the tracheostomy stoma covering device of this invention, and which shows a cut-away view of a border portion of the front panel of the encasement member to illustrate the malleable strip means located therein.

Figure 1:
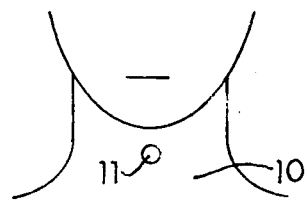
FIG. 1 is a frontal view of a person with a stoma as a result of a tracheostomy.

Referring to FIG. 1, a person 10 is there shown having a stoma or opening 11 at the anterior, lower neck. The stoma 11 is the result of a surgical tracheostomy procedure, which is part of a lyryngectomy, for example. The result of this surgical procedure is that the person 10 has a permanent connection of the trachea or windpipe to the outside, and it is through this opening 11 that respiration takes place. Because person 10 no longer has the use of the nose or mouth for breathing purposes, the lack of air filtering, and air conditioning purposes, from a moisture and heat transfer standpoint, discomfort, coughing and increased likelihood of infection susceptibility often results. Thus, covering and filtering devices are utilized.

Figure 2:
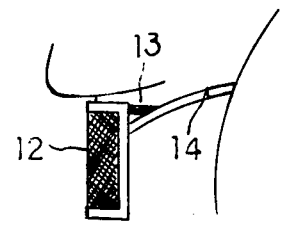
FIG. 2 is a lateral view of a tracheostomy stoma covering device of this invention secured about the neck of a user.

FIG. 2 illustrates a tracheostomy stoma covering device 12 located about a wearer's neck to cover the stoma. The device 12 is shown as a flexible device which is secured about the neck by strap means 14, which utilizes an elastic portion 13 for user comfort. As shown, the strap 14 extends generally diagonally upward from the device body, and this strap configuration is to ensure the upward position of the device body to properly cover the stoma.

FIG. 3 illustrates one embodiment of device 12, and, particularly, it shows the various portions or elements which make up or which can be utilized with the device. The device shown is of a rectangular configuration, however, this particular configuration is not required (i.e., rounded corners or a rounded configuration is also usable so long as the stoma is properly covered). A front panel 20 and a rear panel 21 when secured or fastened together provide the encasement member of the invention. The well known Velcro fastener system is shown utilized on this embodiment of the invention. For example, 27 indicates the top interior fastener strip on the interior of front panel 20, while 37 and 38 (FIG. 4) illustrates the mating portions of the Velcro system located on the back panel 21. The Velcro fastener parts are secured to the interior of front panel 20 borders 22, 23, 24 and 25, while their respective mating parts are secured to the facing interior of back panel 21 borders 31, 32, 33 and 34. And, once secured, the Velcro fastener system provides the access means to the interior of the encasement member. Optionally, other access means are also possible, for example, the use of zippers, snaps, or the like.

The border portions or segments, i.e., 22, 23. etc., are preferrably constructed of a washable material or folded bias tape made of cotton, synthetic materials, such as polyester, combinations of both, or the like. And, the fastening means for the construction of the panels can be stitching 26, as shown in FIG. 3, or water resistent adhesive materials.

Additionally shown are mesh or flexible screen portions or sheet-like materials 19 and 35, respectively, within the borders of front panel 20 and rear panel 21. Although in the drawings this mesh is not shown to extend from border to border, for graphic purposes, the mesh or screen portions should in fact do so, as illustrated in FIG. 2. These mesh or screen portions provide for the filtering of large particles, and, particularly, provide for the passage of air therethrough to the other elements held thereby within the encasement member.

The front panel 20, shown in FIG. 3, is totally separable from the rear or back panel member 21. This embodiment permits a wearer to have a plurality of front panel members 20, all in different colors (i.e., borders and mesh in green, yellow, white, etc.) for use with one rear panel member 21 to form the encasement member. This embodiment permits the user to select a front panel color to match the clothing worn so that the device becomes inconspicuous from a color standpoint. Additionally, other elements used in the encasement member, i.e., foam member 28, can also be in a variety of colors for this reason.

Additionally shown in FIG. 3 are elements provided for use within the encasement member. They include a washable, foam, heat absorbing and releasing element 28, an air filter means 29, and a moisture retention and transfer means or element 30. These elements are all flexible in nature for comfort of the wearer. And, preferably, elements 28 and 30 are washable in character. The air filtering means 29, such as filter paper, is preferably disposable on a daily basis, for example. Thus, the entire covering device is easily maintained from a hygienic standpoint.

Extending from the rear panel 21 are straps 14 and 16. As shown, the individual straps extend generally diagonally from the respective side borders 33 and 34. This diagonal arrangement permits the user to fasten the device about the neck by means of mating fastener elements 17 and 18 located at their respective ends. The fasteners shown are of the Velcro fastener type, and the use of one mating portion being relatively longer than the other, permits the strap means to fit about a wide range of neck sizes. The element 18, as shown, is longer than its corresponding mate 17. Additionally provided, are elastic elements 13 and 15 which extend outwardly from the top border 31, and which attach to the respective straps 14 and 16. The elastic segments permit a comfortable and secure fit of the device about the user's neck, and permit the device wearer to freely rotate and bend the neck without impairing the position of the encasement member relative to the stoma.

FIG. 4 illustrates another embodiment of the tracheostomy stoma covering device. As referred to above, the united front and back panels comprise the encasement member. To that end, it is not absolutely necessary for the front and back panels to be separable and distinct portions. It is only necessary that for purposes of the invention for the encasement member to have access thereinto. And, this can be effectuated by providing an otherwise sewn together front and back panel with Velcro fasteners at at least a portion of one of its borders. It is only necessary for a user to have access into the encasement member to exchange filter means, conditioning elements, or to add to or subtract from these the totality of these elements. Thus, FIG. 4 shows two of the encasement member borders 33 of the rear panel and 24 of the front panel being attached. However, other borders could also be attached.

Additionally shown by the cut-away view of FIG. 4 are the formable or malleable elements 40 and 41, which are shown located at the interior of top and side borders. Stitching 39 is provided to prevent the side element 41 from sliding downward. These metal strips, or stayes, made of aluminum, for example, permit a user to fit or mold the encasement member to the particular contour of the neck. This provides a seal to ensure that all the air inhaled through the stoma is properly filtered and conditioned. Also, the malleable strips provide for a stiffener element function to the encasement member borders to prevent that member from being drawn into the stoma during inhalation, and, thus, providing a hazard to the wearer.

It should be pointed out, that the malleable strips could as well be secured into the border portions of the back panel member 21. And, this arrangement would be preferable in the embodiment shown in FIG. 3, particularly when the rear panel member is used in conjunction with a plurality of various colored front panel members.

As discussed above, the air conditioning element 28 is primarily for the purpose of providing a heat transfer function. And, that the element 30 is primarily for the purpose of providing a moisture transfer function. However, these elements can be combined for functionality, depending upon the nature of the element construction and upon the existing environmental conditions. It has been found that plastic foam materials are well suited for the moisture and heat transfer functions. And, by selecting foam elements, made of varying plastic foam substances, having varying densities, and varying thicknesses, the amount of heat and moisture transfer can be easily controlled by the user. Thus, depending upon time of year, the particular location of the user, indoor or outdoor, by noting the temperature and humidity, the user can easily remove, exchange, or add through the access means of the encasement member, the proper element 28 or 30, or combination thereof.

The moisture transfer element 30 is generally a large cell, or low cell density synthetic foam material which readily permits the passage of air, while retaining moisture for subsequent transfer and for protecting the moisture sensitive filter paper 29. However, this element 30 would not be necessary should the filter paper have a moisture resistant exterior coating to ensure its integrity. However, the element 30, large cell structure, also exhibits heat transfer ability, which during Summer would be sufficient. During Winter, however, a small cell, high cell density element 28 would be necessary for purposes of preventing user discomfort.

It is important to note, that although three elements are shown in the drawings, namely, 28, 29 and 30, elements 28 and 30 are of like material and perform similar functions. In fact, the same foam sheet could be utilized to perform both functions (i.e., one sheet folded in half about one sheet of filter paper; this configuration would also serve to secure the paper). However, they are not necessary for placement in the encasement member under certain conditions. And, their respective placements, are also variable therein depending upon the nature of the air filter means. Although the synthetic foam materials are generally not strong from a tensile strength standpoint, it would be possible, should such be developed, to utilize this material in place of the flexible mesh portions of the front and back panel members. In the latter configuration, the material placed in the front panel could also be suitably colored to match the clothing of the wearer.

It has been found that a device having an encasement member dimension of 4½ inch width, a 6½ inch length, and having a mesh of nylon or other washable fabric with about 16 mesh/inch is well suited for use. In conjunction therewith, straps of approximate 8 inch length each, have been found well suited for a wide range of neck dimensions. However, the configuration of the encasement member and the dimensions described in connection therewith are merely illustrative of the teachings of this invention.

As many changes are possible to the embodiments of this invention, utilizing the teachings of the invention, the description above, and the accompanying drawings, should be viewed in the illustrative, and not in the limited sense.

That which is claimed is:

1. A flexible air filtering and conditioning device for covering a tracheostomy stoma and for securement about the lower anterior neck of a wearer, comprising:
   a. a washable encasement member having parallel, coextensive front and back panels having peripheral, structural portions and having flexible, air permeable mesh portions extending therebetween for permitting the passage of air therethrough, said peripheral structural portions of each said front and back panel including opposing upper side border portions, said encasement member further having openable and closable access means thereinto comprised of Velcro fasteners facingly and matingly secured to at least a segment of said peripheral structural portions of said front and back panel,
   b. flexible and washable strap means for securing said device about the neck of a user, said strap means extending from generally said upper opposing side portions of one said panel members and being fastened thereto, said strap means further having adjustable fastener means at the ends thereof; and,
   c. air filter means for placement within said encasement member for filtering the air passing therethrough.

2. The air filtering and conditioning device of claim 1, wherein said air filter means is comprised of a flexible sheet of disposable filter paper, said sheet of filter paper being replaceable through said access means of said encasement member.

3. The air filtering and conditioning device of claim 1, wherein said device has a flexible, washable, heat and moisture absorbing, retaining and releasing, air permeable foam member for coextensive placement with said air filter means within said encasement member.

4. The air filtering and conditioning device of claim 3, wherein said foam member is positioned between said back panel and said air filter means within said encasement member.

5. The air filtering and conditioning device of claim 1, wherein said adjustable fastener means of said strap means is comprised of mating Velcro fastener members, and wherein one said mating members is substantially longer than said other mating member so that said strap means is usable about a range of user neck sizes.

6. The air filtering and conditioning device of claim 1, wherein said openable and closable access means of said encasement member additionally serves as panel attachment means, whereby said front and back panel members are totally separable and removable from each other.

7. The air filtering and conditioning device of claim 6, wherein said front panel member is constructed of colored, flexible mesh material to match the clothing of a wearer, and, whereby, a wearer can utilize one of a plurality of different colored front panel members in conjunction with the remaining portions of said device to continually match varying clothing color schemes so that the device becomes inconspicuous when worn.

8. The air filtering and conditioning device of claim 6, wherein said access means comprises oppositely positioned, mating Velcro fastening members, said mating Velcro members being fastened to interior, peripheral portions of said front and back panel members.

9. The air filtering and conditioning device of claim 1, wherein said flexible mesh portions comprise a material selected from the group of cotton, nylon or polyester material, and, wherein said mesh ranges from 3 to 20 mesh/inch.

10. The device of claim 1, wherein said strap means includes an elastic portion to permit free movement of a user's neck without displacing the encasement member relative to the stoma.

11. The device of claim 1, wherein said peripheral structural portions of said front and back panels includes a generally horizontal upper border portion, and wherein stiffening members are attached to said horizontal upper border and to said opposing upper side border portions of one of said panels of said encasement member.

12. An air filtering and conditioning device for externally covering a tracheostomy stoma, said device comprising a washable and generally flexible encasement member having generally parallel and coextensive front and back panel members, openable and closable access means operably connected with said panel members to permit internal accessibility into said encasement member, said panel members further having peripheral structural portions including upper side portions and having generally superposed coextensive air permeable, flexible sheet portions disposed between said panel members to filter and condition the air passing therethrough, and, flexible and adjustable securement means for fastening said device about a wearer's neck with said encasement member positioned over a tracheostomy stoma, said securement means having opposing strap members, with fastening means at one end, and being fastened to and extending from said back panel in a diagonal, upward position from the opposing upper peripheral side portions thereof.

13. The device of claim 12, wherein said strap means of the adjustable securement means has a mating Velcro fastener at the ends thereof, and wherein one of the mating members is substantially longer than the other.

14. The device of claim 12, wherein said peripheral structural portions of one said panel members has at least one malleable strip attached thereto for fitting the encasement to the contour of a user's neck.

15. A flexible air filtering and conditioning device for covering a tracheostomy stoma and for securement about the lower anterior neck of a wearer, comprising:
a. a washable encasement member having parallel, coextensive front and back panels having peripheral, structural portions and having flexible, air permeable mesh portions extending therebetween for permitting the passage of air therethrough, said flexible mesh portions further comprising a material selected from the group of cotton, nylon and polyester material and having a mesh count ranging from three to twenty per inch, said peripheral structural portions of each said front and back panel including opposing upper side border portions, said encasement member further having openable and closable access means operably connected with said panels to permit internal accessibility thereinto,
b. flexible and washable strap means for securing said device about the neck of a user, said strap means extending from generally said upper opposing side portions of one said panel members and being fastened thereto, said strap means further having adjustable fastener means at the ends thereof, and,
c. air filter means for placement within said encasement member for filtering the air passing therethrough.

16. The device of claim 15, wherein said air filter means is comprised of a flexible sheet of disposable filter paper being coextensive said mesh portions of said front and back panels and being replaceable through said access means of said encasement member.

17. The device of claim 15, wherein said encasement member is generally rectangular in configuration.

18. The device of claim 15, wherein said encasement member further has a flexible and washable air permeable foam member disposed therein generally coextensive said mesh portions of the front and back panels.

19. The device of claim 15, wherein said adjustable fastener means of the strap means is comprised of a mating Velcro fastener, and wherein one of the mating members is substantially longer than the other.

20. The device of claim 15, wherein said peripheral structural portions of one said panel member has at least one malleable strip attached thereto for fitting the encasement member to the contour of a user's neck.

* * * * *